US00PP37437P2

(12) United States Plant Patent
Ranney et al.

(10) Patent No.: US PP37,437 P2
(45) Date of Patent: May 26, 2026

(54) ***ELAEAGNUS* PLANT NAMED 'NCEX1'**

(50) Latin Name: ***Elaeagnus pungens* x *Elaeagnus* x *ebbingei***
Varietal Denomination: NCEX1

(71) Applicant: North Carolina State University, Raleigh, NC (US)

(72) Inventors: Thomas Green Ranney, Arden, NC (US); Andra Windorf Nus, Arden, NC (US); Irene Palmer, Arden, NC (US); John Tyler Nix, Arden, NC (US); Darren H. Touchell, Arden, NC (US); Nathan P. Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/245,286

(22) Filed: Jun. 21, 2025

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

(56) References Cited

PUBLICATIONS https://digitaleditions.walsworth.com/publication/?i=827804&p=72&view=issueViewer; 2024; 2 pages.*

* cited by examiner

*Primary Examiner* — Kent L Bell

(57) ABSTRACT

A new and distinct cultivar of *Elaeagnus* plant named 'NCEX1' is disclosed, characterized by evergreen, showy silver foliage, fragrant flowers, and a rounded, compact plant habit. 'NCEX1' is a triploid cytotype producing seedless fruit, or infrequently fruit with a small amount of non-viable seed. Plants of the new cultivar are thornless. The new cultivar is an *Elaeagnus*, normally used for outdoor ornamental purposes.

3 Drawing Sheets

Latin name of the genus and species: *Elaeagnus pungens* x *Elaeagnus* x *ebbingei*.

Cultivar denomination: 'NCEX1'.

BACKGROUND OF THE INVENTION

The new *Elaeagnus* cultivar is a product of a planned breeding program conducted by the inventor to develop sterile and seedless *Elaeagnus* cultivars. The seed parent was the unpatented *Elaeagnus pungens* 'H2005-051-008' (internal, induced tetraploid). The pollen parent was the unpatented *Elaeagnus* x *ebbingei* 'Gilt Edge'. The cross resulting in this new cultivar was made during Spring 2008 in Mills River, North Carolina. The new cultivar was identified as a potentially interesting selection in the Summer of 2009, at a research nursery in Mills River, North Carolina.

Asexual propagation of the new cultivar 'NCEX1' by vegetative cuttings was first performed during October of 2012 at a research nursery in Mills River, North Carolina. Subsequent propagation has shown that the unique features of this cultivar are stable and reproduced true to type in three successive propagation cycles.

Plants of the new cultivar were first disclosed to third parties Jun. 25, 2024, in the United States. Plants were shown at an invitational event in Grand Haven, MI. This disclosure was made directly by the inventor or one who obtained the claimed invention directly or indirectly from the inventor. This and all public disclosures made between Jun. 25, 2024, and the filing of this application fall within the exception allowed under 102(b)(1).

SUMMARY OF THE INVENTION

The cultivar 'NCEX1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCEX1'. These characteristics in combination distinguish 'NCEX1' as a new and distinct *Elaeagnus* cultivar:

1. A triploid cytotype that produces seedless (or infrequently a small amount of non-viable seed) fruit.
2. Fragrant flowers.
3. Evergreen with showy silver foliage.
4. Rounded, compact habit that does not produce long trailing shoots.
5. Thornless.

PARENT COMPARISONS

Plants of the new cultivar *Elaeagnus* 'NCEX1' are similar to plants of the seed parent in most horticultural characteristics; however, plants of the new cultivar 'NCEX1' differ in the following:

1. The new cultivar is a triploid cytotype, while the seed parent is a tetraploid cytotype.

2. Plants of the new cultivar are thornless, while plants of the seed parent have thorns.
3. Plants of the new cultivar are female infertile, while plants of the seed parent are female fertile.

Plants of the new cultivar *Elaeagnus* 'NCEX1' are similar to plants of the pollen parent in most horticultural characteristics; however, plants of the new cultivar 'NCEX1' differ in the following:

1. Foliage color of the new cultivar is green silver, while the foliage color of the pollen parent is variegated yellow and green.
2. Plants of the new cultivar are female infertile, while plants of the pollen parent are female fertile.

COMMERCIAL COMPARISON

Plants of the new cultivar 'NCEX1' are comparable to the commercial cultivar *Elaeagnus* x *ebbingei* 'Ebbinge's Silverberry', unpatented. The two *Elaeagnus* cultivars are similar in most horticultural characteristics, however, the new cultivar 'NCEX1' differs in the following:

1. Plants of the new cultivar are female sterile, while plants of this comparator are female fertile.
2. Plants of the new cultivar are smaller at maturity than plants of this comparator.
3. Plants of the new cultivar do not produce long trailing shoots, while plants of this comparator do produce long trailing shoots.

BRIEF DESCRIPTION OF THE PHOTOGRAPHS

This new *Elaeagnus* is illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new *Elaeagnus*.

DETAILED BOTANICAL DESCRIPTION

Figure 1:
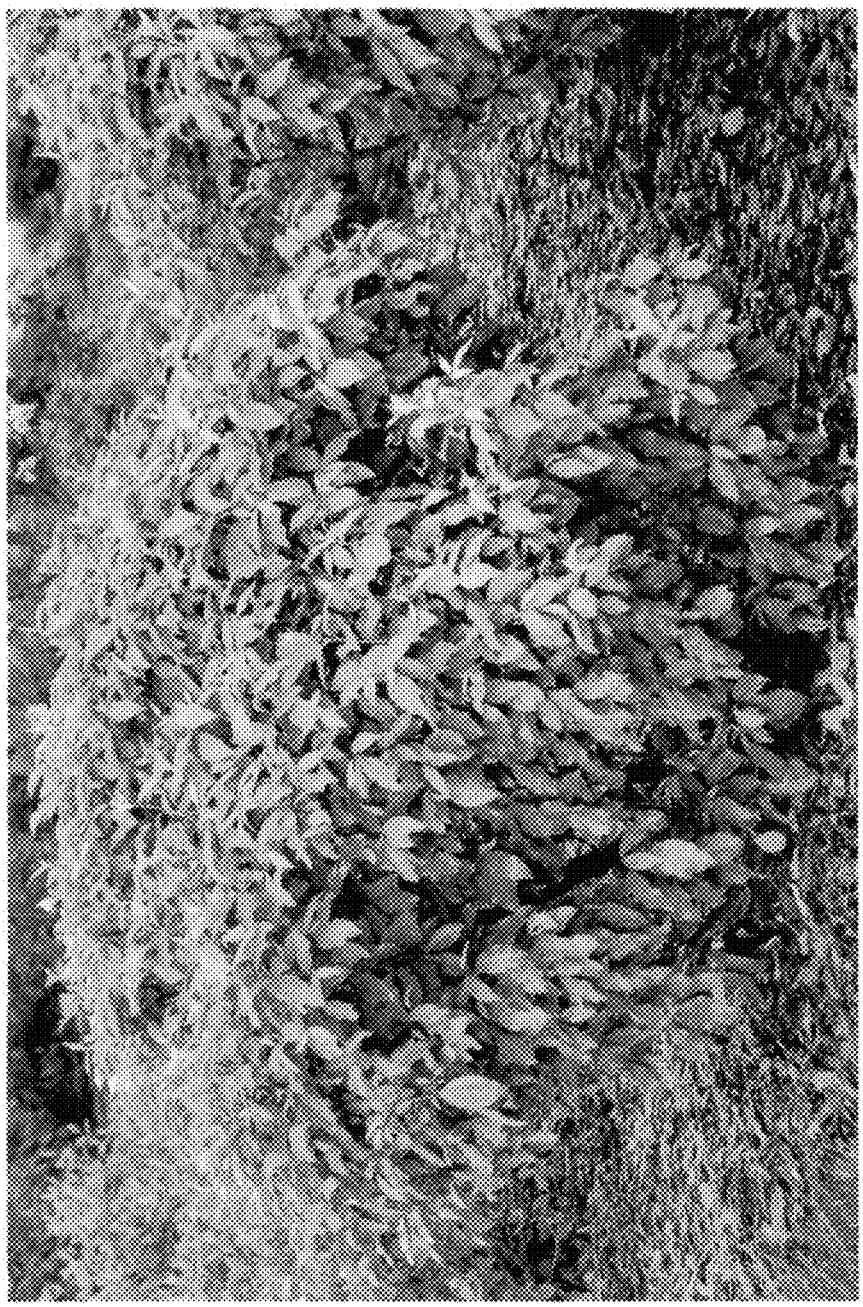
FIG. 1 is a color photograph showing the habit of a ten-year old field-grown plant in fall of 2022 in Mills River, North Carolina.
Figure 2:
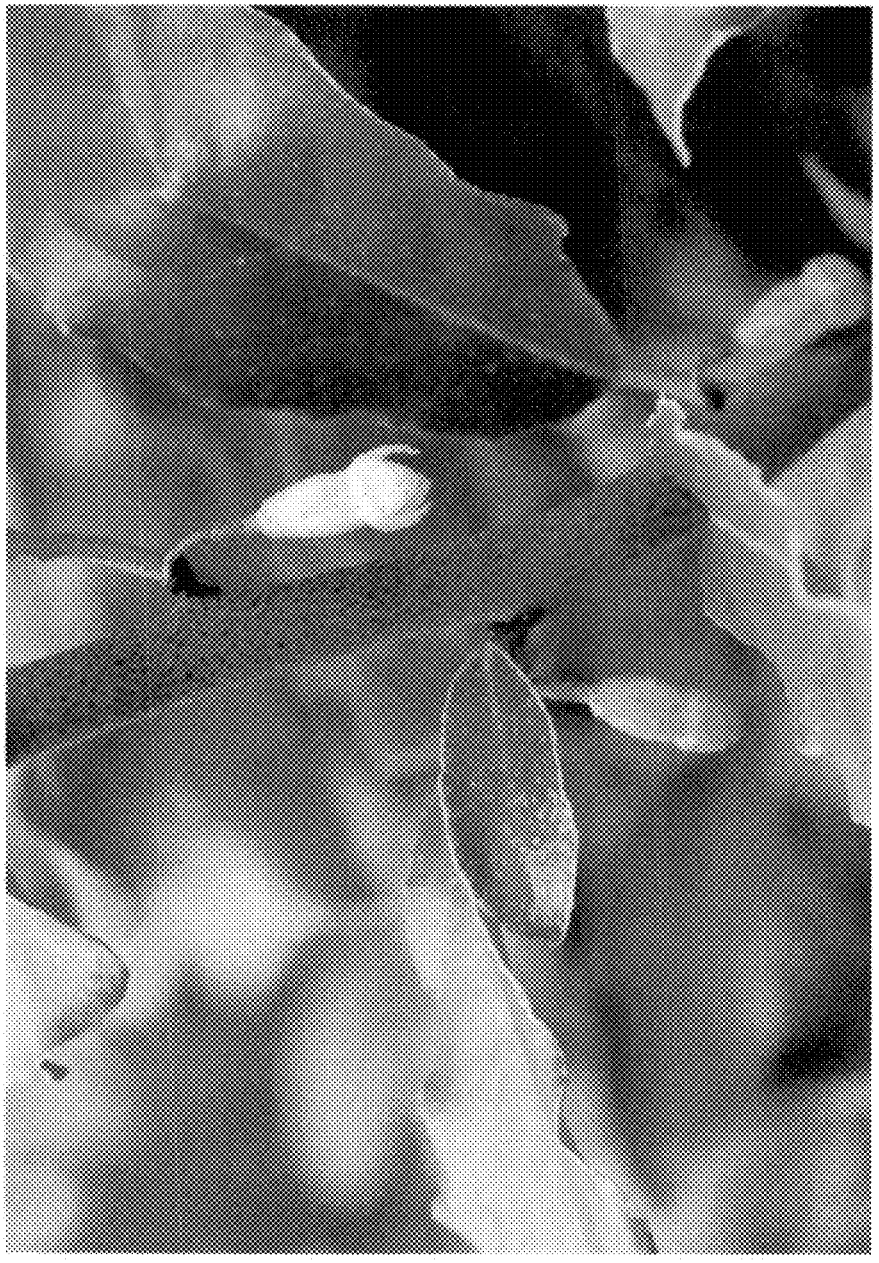
FIG. 2 is a photograph of the flower of a ten-year old field-grown plant in fall of 2022, in Mills River, North Carolina.
Figure 3:
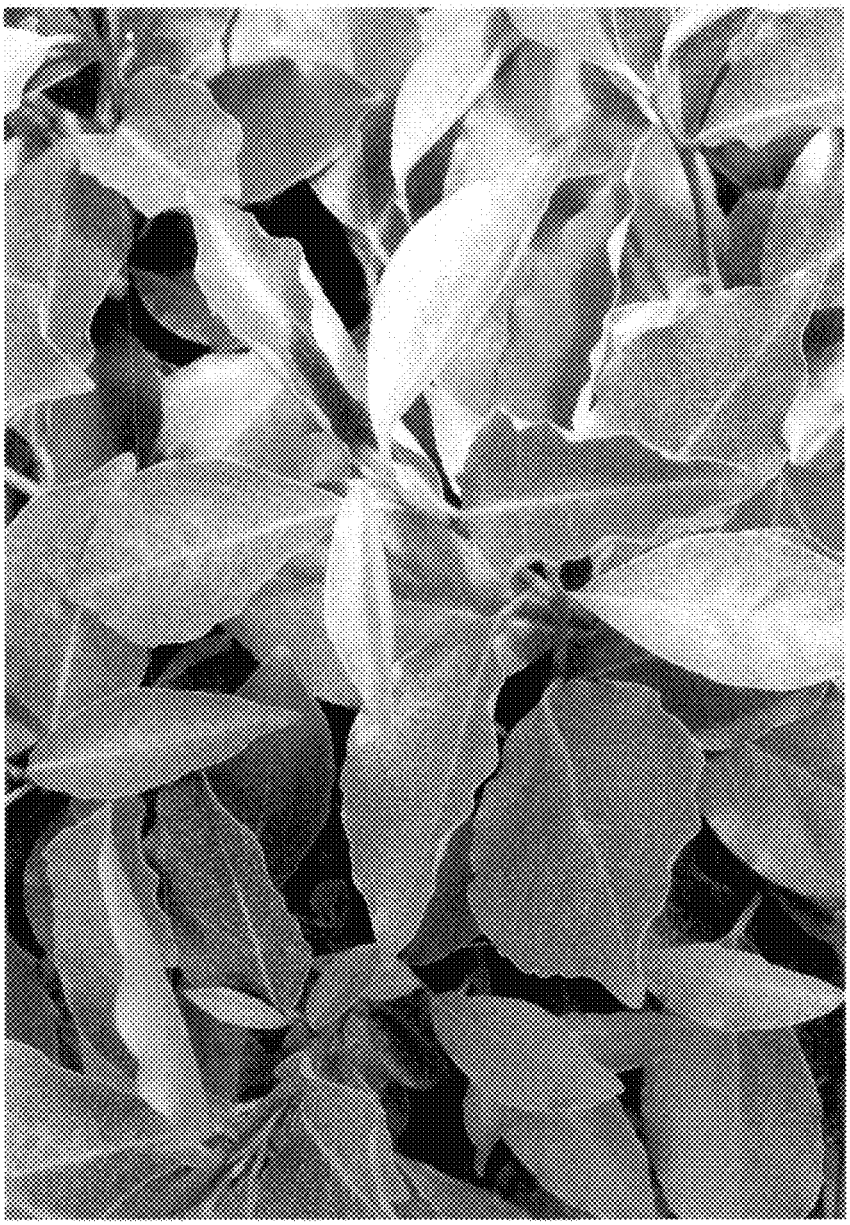
FIG. 3 is a color photograph showing the silver foliage of a ten-year old field-grown plant in fall of 2022 in Mills River, North Carolina.

The following is a detailed description of the botanical characteristics of the new and distinct *Elaeagnus* cultivar known by the denomination 'NCEX1'. The detailed description was taken on a seven-year-old field-grown plant in 2022 in Mills River, North Carolina. All colors cited herein refer to The Royal Horticultural Society Colour Chart (The Royal Horticultural Society (R.H.S.), London, 2015, Sixth Edition). Where specific dimensions, sizes, colors, and other characteristics are given, it is to be understood that such characteristics are approximations or averages set forth as accurately as practicable.

Botanical classification: *Elaeagnus* 'NCEX1'.

PROPAGATION

Type of propagation typically used: Softwood cuttings.
Time to produce a rooted plantlet: 8 to 10 weeks.

PLANT

Age of plant described: 7 years.
Plant type: Flowering tree.
Growth habit: Rounded, compact.
Plant spread: 200 cm.
Plant height: 240 cm.
Stems, shoots, branches:

*Shoots* (*current year's growth*).—Shoot length: Average 13 cm (range 9 to 19 cm). Shoot diameter: About 0.2 cm. Color: RHS Reddish-Brown 177A. Texture: Scaly.

*Shoots* (*prior year's growth*).—Stem length: About 20 cm. Stem diameter: About 0.5 cm. Color: RHS Olive-Grey 197A. Texture: Scaly.

*Branches* (*woody branches* 2-4 *years old*).—Branch length: Average 34 cm (24 to 40 cm). Branch diameter: Average 1.1 cm (0.6 to 1.6 cm). Color: RHS Brown N199B. Texture: Scaly.

Quantity of primary branches: 5 to 7.
Quantity of lateral branches: 10 to 20 per primary branch.
Internode length: Average 1.8 cm (1 to 4 cm).
Root description: Main roots woody, lateral roots fin and fibrous. Older roots brown, emerging young root tan to white. Not accurately measured with a color chart as the roots are stained with soil.

FOLIAGE

Leaf:

*Type*.—Simple.
*Persistence*.—Evergreen.
*Arrangement*.—Alternate.
*Shape*.—Elliptical.
*Length of lamina*.—Average 6 cm (4.9 to 6.8 cm).
*Width*.—Average 3 cm (2.5 to 3.5 cm).
*Apex*.—Acute.
*Base*.—Rounded.
*Margin*.—Entire, wavy.
*Color, emerging foliage*.—Upper Surface: Covered with silvery scales of RHS Yellowish-Grey 198D and dotted with Brown 165A scales. Lower Surface: Covered with silvery scales of RHS Yellowish-Grey 198D and dotted with Brown 165A scales.
*Color, mature foliage*.—Upper Surface: RHS Green 137B. Lower Surface: Covered with silvery scales of RHS Yellowish-Grey 198D and dotted with Brown 165A scales.
*Texture*.—Glabrous, lustrous upper and lower surfaces.
*Venation*.—Pinnate.
*Vein color, upper surface*.—RHS Yellow-Green 146C.
*Vein color, lower surface*.—Covered with RHS Brownish-Orange 164A scales at the base, and Yellowish-Grey 198D scales at the tip.
*Leaf attachment*.—Petiolate.

Petiole:

*Length*.—About 1 cm.

*Diameter*.—About 0.1 cm.

*Color*.—RHS Brownish-Orange 164A.

*Texture*.—Scaly.

FLOWER

Inflorescence:

*Description*.—One to three perfect, apetalous flowers in the leaf axils.

*Number of flowers per inflorescence*.—1.

*Fragrance*.—Sweet.

*Flowering season*.—October to November in Mills River, NC.

*Diameter*.—Average 1.6 cm (1.5 to 1.8 cm).

*Height*.—Average 1.3 cm (1.2 to 1.4 cm).

Flower:

*Shape*.—Tubular.

*Aspect*.—Pendulous.

*Diameter*.—About 0.6 cm.

*Height*.—About 1 cm.

Sepals:

*Number*.—4 sepals.

*Shape*.—Fused into a tube at base with flared lobes.

*Length*.—About 1 cm.

*Width*.—About 0.4 cm.

*Margin*.—Entire.

*Apex*.—Acute.

*Base*.—Fused.

*Color upper and lower surfaces*.—RHS White 155D with sporadic Brownish-Orange 164A scales.

*Texture*.—Scaly all surfaces.

Peduncle:

*Length*.—About 0.5 cm.

*Diameter*.—Less than 0.1 cm.

*Color*.—RHS Yellowish-Grey 198D with sporadic Brownish-Orange 164A scales.

*Texture*.—Scaly.

REPRODUCTIVE ORGANS

Gynoecium:

*Pistil number*.—1.

*Pistil length*.—About 1.5 cm.

*Stigma shape*.—Rounded.

*Style length*.—About 1 cm.

*Style width*.—Less than 0.1 cm.

Androecium:

*Stamen number*.—4 with filament fused to sepal.

*Anther shape*.—Elliptical.

*Anther length*.—About 0.2 cm.

*Anther width*.—About 0.1 cm.

FRUIT AND SEEDS

Fruit:

*Type*.—Drupe.

*Length*.—About 1.8 cm.

*Width*.—About 1 cm.

*Color*.—RHS Orange 167A.

*Texture*.—Scaly.

*Seed*.—Most fruits are seedless; infrequently a small amount of shriveled non-viable seed is produced.

OTHER CHARACTERISTICS

Disease and insect resistance: No significant disease or insect pests have been observed.

Cold hardiness: At least USDA zone 6b; testing has not been completed in colder zones.

DNA content: Relative 2C hololoid DNA contents were determined following methods provided by Ranney et al. (2018) using DAPI fluorochrome and *Pisum sativum* 'Ctirad' (unpatented) as an internal standard with a 2C DNA content of 8.66 pg (Nix et al., 2024). DNA content for 'NCEX1' was 3.10±0.02 SEM pg.

What is claimed is:

1. A new and distinct cultivar of *Elaeagnus* plant named 'NCEX1' as herein illustrated and described.

* * * * *